United States Patent [19]
Flint et al.

[11] Patent Number: 4,815,842
[45] Date of Patent: Mar. 28, 1989

[54] SPECTROGRAPH FOR EVALUATING CONTAMINATION OF OPTICAL COMPONENTS IN SPACE

[75] Inventors: Bruce K. Flint, Wolfebro, N.H.; Robert D. Fancy, Oakdale; Robert V. Jarratt, Jr., Groton, both of Mass.

[73] Assignee: Acton Research Corporation, Acton, Mass.

[21] Appl. No.: 868,798

[22] Filed: May 29, 1986

[51] Int. Cl.$^4$ .......................... G01N 21/13; G01J 3/32
[52] U.S. Cl. .......................... 356/73; 356/328; 356/244
[58] Field of Search .................. 356/73, 244, 328, 445, 356/446, 447, 448

[56] References Cited

U.S. PATENT DOCUMENTS

| | | | |
|---|---|---|---|
| 3,532,428 | 10/1970 | Coogan | 356/300 |
| 3,687,519 | 8/1972 | Mapes | 356/73 |
| 4,040,750 | 8/1977 | Zwiener | 356/448 |
| 4,640,617 | 2/1987 | Hughes et al. | 356/244 X |

FOREIGN PATENT DOCUMENTS

52-71287  6/1977  Japan ................................. 356/448

*Primary Examiner*—Vincent P. McGraw
*Attorney, Agent, or Firm*—James H. Grover

[57] ABSTRACT

A monochromatic spectrometer for evaluating contamination changes in the surface condition of lenses, reflectors and similar optical samples in the vacuum of a space mission includes a vacuum ultraviolet beam source redirected from a dispersion grating through a test station and reflected from a mirror to a photodetector. A rotatable carrier supports two or more optical samples, both transmissive and reflective and selectively positions one sample at a time at the test station so that the selected sample modifies the VUV beam according to its surface condition. The mirror is movable from a first position in which it reflects the beam transmitted through a sample to second position in which it reflects the beam reflected from a sample. The sample condition measured by the photodetector, the position of the rotatable carrier and mission elapsed time are recorded in a memory for re-transmission or later read out.

26 Claims, 1 Drawing Sheet

SPECTROGRAPH FOR EVALUATING CONTAMINATION OF OPTICAL COMPONENTS IN SPACE

BACKGROUND OF THE INVENTION

Optical instruments with reflective and refractive components such as coated mirrors and lenses are subject to contamination when used in space environments aboard the shuttle spacecraft, satellites and research rockets. Typical space experimental instruments operate in or near the vacuum ultraviolet wavelengths, and include a telescope, a spectrometer and photodetector with six or more optical surfaces.

A relatively small loss in reflectivity and transmission of each surface could result in either huge uncertainties in the data recovered or, even worse, the loss of meaningful data due to greatly reduced instrument sensitivity. Surface contamination of the optical components may result, even in the vacuum of space, from outgassing and subsequent deposition of hydrocarbons et al on the optical surfaces, bombardment by particles and chemical etching. Some of the surface contamination is reversible; a mirror may degrade when cold, then outgas volatile contaminants when heated by exposure to the sun; and generally, degradation is not linear with time so that measuring the efficiency of the surfaces at the beginning and at the end of a mission will not accurately determine the efficiency of the instrument at the time experimental data was taken.

It is the object of the present invention to provide spectrometric apparatus which will accompany experimental optical instruments on a space mission and measure the degradation of their optical components during their experiment.

SUMMARY OF THE INVENTION

According to the invention apparatus for evaluating the surface condition of optical samples comprises a light source emitting a beam; spectral dispersing means redirecting the light beam on a test path; means to support optical samples in the test path so that the samples modify the light beam according to the condition of their respective surfaces; a photodetector for measuring the intensity of the modified beam; and a mirror for reflecting to the photodetector light received from the sample in the test path; wherein the optical support means includes a movable carrier selectively positioning one sample at a time at a test station in the test path, and the apparatus includes means for moving the mirror from a first position in the test path at one side of the test station to a second position on the opposite side of the test station; whereby both the transmissivity and reflectivity of a plurality of optical samples are measured.

In another aspect the support for the optical samples is movable so as to dispose at least one sample outside a housing in which the support is mounted.

DRAWING

DESCRIPTION OF THE SPECIFIC EMBODIMENTS

Figure 1:
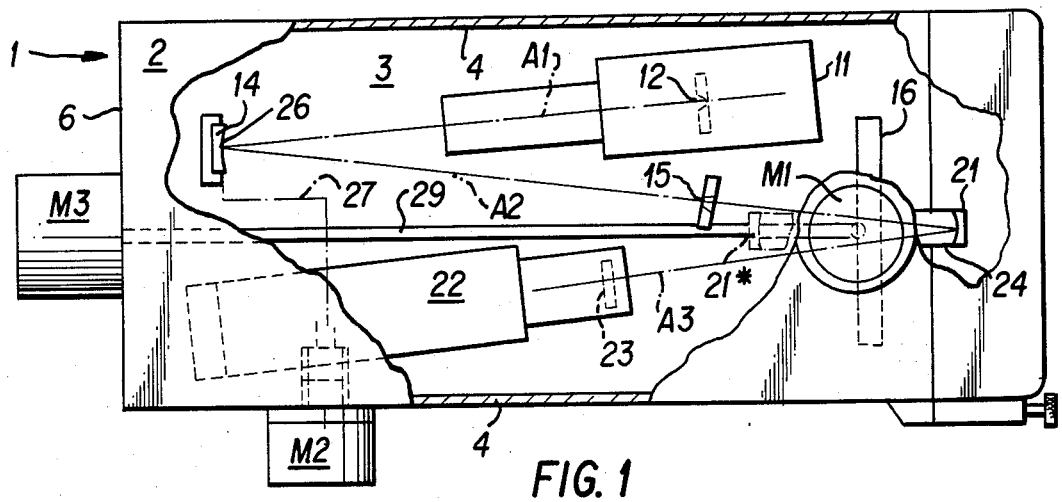
FIG. 1 is a plan view of the optical sample testing apparatus, partly broken away.

The spectrometric contamination evaluating apparatus shown in FIGS. 1 to 4 comprises a housing 1 with a top wall 2, bottom wall 3, side walls 4 and an end wall 6 at one end. An access door 7 closes the opposite end of the housing secured by a lock screw 8. Within the housing is a scanning monochromatic spectrometer, or monochromator, consisting of a vacuum ultraviolet (VUV) light source 11 with an exit slit 12 which directs a VUV light beam in a narrow ribbon along an axis A1 to a holographic refraction grating 14. The grating disperses the beam in a range in the VUV spectrum along a test path A2 through an exit slit to a sample supporting wheel 16.

A narrow wavelength of the spectrally dispersed beam is incident on an optical component on the wheel at a test station 17. If the component is transmissive, as a lens, the test beam is attenuated by the sample according to its surface condition, and then reflected by a concave focussing mirror 21 on a third path A3 to a photodetector 22 with a photocathode 23 which measures the VUV photon intensity or energy of the transmitted test beam.

A suitable light source 11 is a sealed Deuterium lamp with a magnesium fluoride window having a one millimeter exit slit acting as the entrance slit to the monochromator. The spectral dispersion is effected by a 200 millimeter radius, 1800 G/mm holographic grating optimized for wavelengths from 120 to 210 nonometers. Both the grating 14 and concave mirror 21 are coated for maximum reflectivity at 120 nm. A preferred photodetector is an EMR 541F photomultiplier tube, distributed by EMR Photoelectric, Princeton, N.J.

Figure 2:
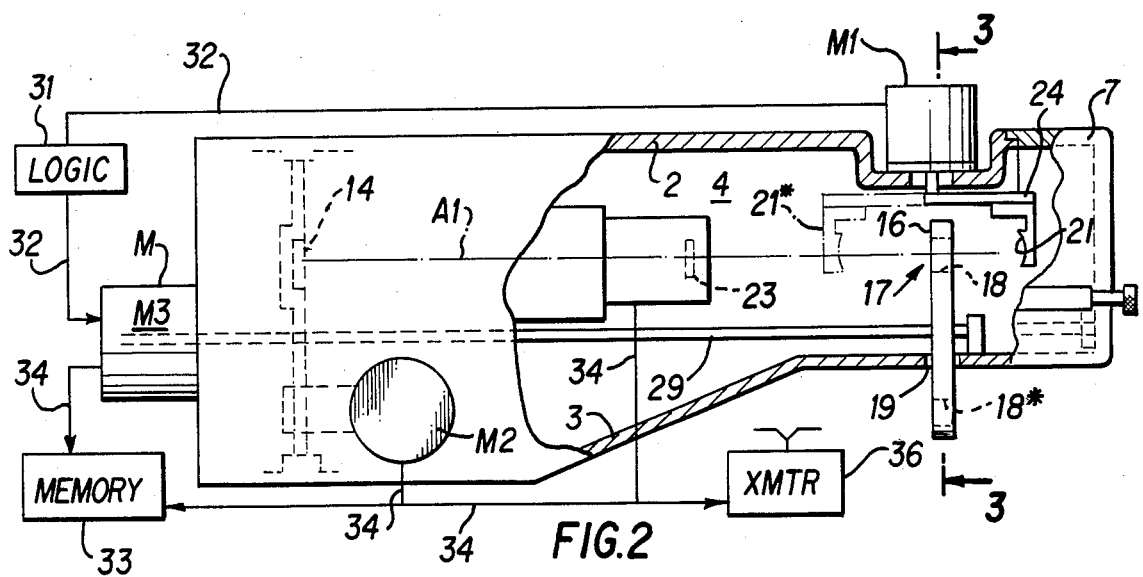
FIG. 2 is a plan view of the apparatus, partly broken away and showing associated electronic apparatus diagrammatically.
Figure 3:
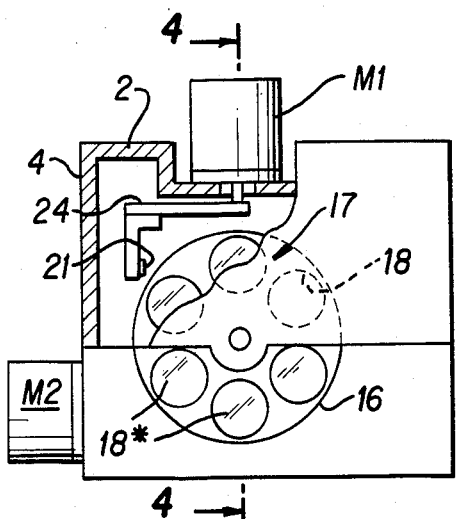
FIG. 3 is a section on line 3—3 of FIG. 2.

The component supporting wheel 16 has a plurality of circular openings 18 for holding lenses and mirrors and rotating them to the test station M in the test path A2. One of the openings is left unfilled for calibration. As shown in FIGS. 2 and 3 optical components may be shielded within the housing 1 from the ambient environment, or moved through a slit 19 outside the housing to positions 18* exposed to the ambient environment as are the optical components of the other experimental instruments on the mission.

Figure 4:
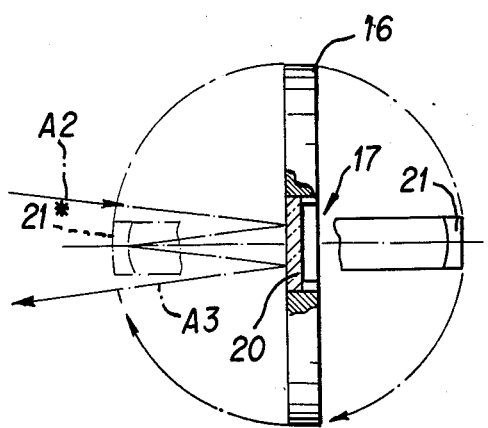
FIG. 4 is a section on line 4—4 of FIG. 3, enlarged twice.

Alternatively to testing transmissive components like lenses the present evaluating apparatus also tests reflective elements at the test station 17 by moving the mirror 21 from the solid line position 21 of FIGS. 1, 2 and 4 to a broken line position 21* on the opposite side of the test station 17. The mirror 21 is supported on a bell crank 24 rotated by a stepping motor Ml. When energized by logic circuits the motor Ml swings the mirror to the broken line position 21*. The displaced mirror and the reflective optical component 20 will then, by double reflection, redirect the test beam on a folded path which resolves on the same axis as the path A3 to the photodetector 22 as did the transmitted test beam.

The grating 14 rotates on a shaft 26 turned by a motor M2 through a linkage 27 such as that shown in U.S. Pat. No. 3,090,863. Its rotation directs successive monochromatic beams to the exit slit throughout the VUV spectrum. The component wheel 16 is turned on a shaft 29 by a stepping motor M3 so as to bring selected optical samples to the test station 17 and also outside the shielding housing 1 into the ambient environment. Energization of all three motors is programmed by computer logic as illustrated by control lines 32 in FIG. 2 to the mirror motor M1 and wheel motor M3. The angular positions of the motors and of the wheel 16, mirror 21 and grating 14 with respect to the same time base as the data sensed by the photometer 23 and other events in the mission are stored in a memory 33 through lines 34. Alternatively these data may be sent through a transmitter 36 to a remote memory or data recorder.

It should be understood that the present disclosure is for the purpose of illustration only and that this invention includes all modifications and equivalents which fall within the scope of the appended claims.

We claim:

1. Apparatus for evaluating the surface condition of optical components comprising:
   a light source emitting a beam;
   spectral dispersing means redirecting the light on a test path;
   means to support optical components in the test path so that the components modify the light beam according to the conditions of their respective surfaces;
   a photodetector for measuring the intensity of the modified beam; and
   a single mirror for reflecting to the photodetector light received from the test path;
in combination with:
   a single housing for the spectral dispersing means, component support means, photodetector and mirror; and
   a moveable carrier constituting the support means and including means to support a plurality of optical components and selectively and successively position the components, one at a time, at a test station in the test path; and
   means for moving the mirror from a first position in the test path at one side of the station to a second position on the opposite side of the test station;
   whereby both the transmissivity and reflectivity of a plurality of optical components are measured by the light source, spectral dispersing means and a single reflector within a single housing.

2. Apparatus according to claim 1 wherein the carrier comprises a wheel rotating on an axis and having a plurality of angularly spaced optical component holders rotatable to a common test station.

3. Apparatus according to claim 2 wherein the light source, spectral disposing means, component support and photodetector are mounted on a common base and the mirror and wheel are rotatably mounted on the base so that the mirror swings around the carrier on an axis normal to the axis of the wheel.

4. Apparatus according to claim 3 including motors for rotating the mirror and wheel respectively.

5. Apparatus according to claim 4 including logic controlling actuation of the motors.

6. Apparatus according to claim 5 including a memory for storing the intensities sensed by the photodetector and the simultaneous angular position of the sample wheel with respect to a common time base.

7. Apparatus according to claim 1 wherein the first position of the mirror is in a path of the light beam transmitted through an optical component.

8. Apparatus according to claim 1 wherein the second position of the mirror is in a folded path of the light beam reflected from an optical component.

9. Apparatus according to claim 1 wherein light in the first position of the mirror, is propogated on a first axis from the source to the dispersing means, thence on a second path through the component in the test station to the mirror, and thence from the mirror to the photodetector.

10. Apparatus according to claim 1 wherein light, in the second position of the mirror, is propagated on a first path from the source to the dispersing means, thence on a second path to the component in the test station, and thence on a folded path, by double reflection between the mirror and component, to the photodetector, so that the surface of the component twice modifies the light beam by two reflections.

11. Apparatus according to claim 1 wherein the spectral dispersing means is a grating.

12. Apparatus according to claim 11 wherein the grating is pivotally mounted to disperse a range of monochromatic light wavelengths to the test station.

13. Apparatus according to claim 11 including a motor rotating the grating through a series of angular positions.

14. Apparatus according to claim 13 including a memory for storing the intensities sensed by the photodetector and the simultaneous angular position of the grating.

15. Apparatus according to claim 1 wherein the light source comprises a light exit slit which forms an entrance slit for emitting the light beam toward the spectral dispersing means.

16. Apparatus according to claim 1 wherein the sample support is mounted in a housing shielding samples from the ambient environment and the sample support is movably mounted on the housing to move samples out of the housing into the environment.

17. Apparatus according to claim 16 including a motor for moving the sample support outside the housing.

18. Apparatus according to claim 1 wherein the light source, spectral dispersing means, component support and photodetector are mounted in a housing shielding them from the ambient environment and the component support is mounted on the housing to move components outside of the housing.

19. Apparatus according to claim 18 including a motor for moving the component support to a position outside the housing.

20. Apparatus according to claim 1 wherein the light source is a deuterium ultraviolet lamp with an exit slit acting as an entrance slit for the path of the light beam to the spectral dispersing means.

21. Apparatus according to claim 1 including a memory for storing the intensities sensed by the photodetector.

22. Apparatus according to claim 1 including radio means for transmitting the intensities sensed by the photodetector to a remote receiving station.

23. Apparatus according to claim 10 wherein the dispersing means, component carrier and detector face each other substantially parallel so as to form small angles between the first, second and folded paths.

24. Apparatus for evaluating the surface condition of optical samples comprising:
   a light source emitting a beam;
   spectral dispersing means redirecting the light beam on a test path;
   means to support optical components in the test path so that the components modify the light beam according to the condition of their respective surfaces;

a photodetector for measuring the intensity of the modification beam; and a mirror for reflecting to the photodetector light received from the sample in the test path;

wherein the optical support means includes a movable carrier for holding two or more components, the carrier being movable to selectively position one component at a time at a test station in the test path, the component support being mounted in a housing shielding components from the ambient environment and movable to dispose at least one component outside the housing.

25. Apparatus according to claim 24 including a motor for moving the support.

26. Apparatus according to claim 24 including a memory for storing the intensities sensed by the photodetector.

* * * * *